United States Patent [19]

Rice

[11] Patent Number: 4,521,601
[45] Date of Patent: * Jun. 4, 1985

[54] PRACTICAL TOTAL SYNTHESIS UNNATURAL ENANTIOMERS OF OPIUM-DERIVED MORPHINANS

[75] Inventor: Kenner C. Rice, Rockville, Md.

[73] Assignee: The United States of America as represented by the Department of Health & Human Services, Washington, D.C.

[ * ] Notice: The portion of the term of this patent subsequent to Jan. 11, 2000 has been disclaimed.

[21] Appl. No.: 477,970

[22] Filed: Mar. 23, 1983

Related U.S. Application Data

[63] Continuation-in-part of Ser. No. 265,469, May 20, 1981, Pat. No. 4,410,700, which is a continuation-in-part of Ser. No. 165,690, Jul. 3, 1980, abandoned.

[51] Int. Cl.$^3$ ............. C07D 489/02; C07D 221/28; C07D 217/20
[52] U.S. Cl. ...................... 546/45; 546/15; 546/44; 546/74; 546/146; 546/149
[58] Field of Search ................. 546/44, 45, 74

[56] References Cited

U.S. PATENT DOCUMENTS

| | | | |
|---|---|---|---|
| 3,438,989 | 4/1969 | Shavel, Jr. et al. | 546/74 |
| 4,003,903 | 1/1977 | Schwartz | 546/44 X |
| 4,368,326 | 1/1983 | Rice | 546/45 |
| 4,410,700 | 10/1983 | Rice | 546/149 |

FOREIGN PATENT DOCUMENTS 7107921 12/1971 Netherlands .
1330581 9/1973 United Kingdom .

OTHER PUBLICATIONS

DeGraw et al., J. Heterocyclic Chem., vol. 11, pp. 363-367 (1974).
Beyerman et al., Recl. Trav. Chim Pays-Bas, 95, pp. 184-188, (1976).
Beyerman et al., Recl. Trav. Chim Pay-Bas, 97, pp. 127-130, (1978).
Beyerman et al., Chemical Abstracts, 91, 74760y (1979).
Anon., Chemical & Engineering News, Jan. 18, 1971, p. 33.
Gesson et al., J. Chem. Soc., Chem. Comm. pp. 652-653 (1976).
Fieser et al., Reagents for Organic Synthesis, vol. 6, John Wiley Sons, New York, 1977, pp. 617-618.
Herlem, Pure & Appl. Chem., vol. 49, pp. 107-113 (1977).
Gesson et al., Chemical Abstracts, vol. 88, 152297g (1978).
Grewe et al., Chem. Ber., 100, 1550-1558 (1967).
Friedrichsen, Chem. Ber., 101, 1190-1194 (1968).
Maeda et al., Chemical Abstracts, vol. 69, 52367u (1968).
Sawa et al., Chemical Abstracts, vol. 73, 131195x (1970).
Hellerbach et al., "Synthetic Analgesics, Part IIA, Morphinans, Pergamon Press, 1966, pp. 1-104.
Birch et al., "Reduction by Metal-Ammonia Solution and Related Reagents," Advances In Organic Chemistry, vol. 8, Wiley-Interscience, 1972, pp. 1-65.
May et al., "Morphine and Its Modifications," Medicinal Chemistry, vol. 5, D. Stephens, Analgesics, 1965, pp. 123-174.
Rice, J. Organic Chem., vol. 45, No. 15, pp. 3135-3137 (07/18/80).

Primary Examiner—Diana G. Rivers
Attorney, Agent, or Firm—John S. Roberts, Jr.

[57] ABSTRACT

This invention relates to compounds which may be described as the unnatural enantiomers of morphine agonists and antagonists, which are useful as antitussives. The synthesis utilized is capable of producing all of the unnatural enantiomers of medically important opium derivatives of the morphinan type, including thebaine.

1 Claim, No Drawings

PRACTICAL TOTAL SYNTHESIS UNNATURAL ENANTIOMERS OF OPIUM-DERIVED MORPHINANS

This application is a continuation-in-part application of pending Ser. No. 265,469 filed May 20, 1981, now U.S. Pat. No. 4,410,700, which is a continuation-in-part of Ser. No. 165,690, filed July 3, 1980, now abandoned, U.S. Pat. No. 4,368,326 describes a process relating to the natural isomers and stems from the above Ser. No. 165,690, now abandoned.

The present application relates to compounds which may be described as the unnatural enantiomers of morphine agonists and antagonists, which are useful as antitussives. The synthesis utilized is capable of producing all of the unnatural enantiomers of medically important opium derivatives of the morphinan type, including thebaine.

Among the advantages of the process is a facile optical resolution of racemic 7 to give (−)-7a and (+)-7a. The former can then be converted as described below to the unnatural enantiomers of all medically valuable opium derived agonists and antagonists and also to related derivatives.

Among the advantages emphasized by the present invention are the utilization of β,γ-unsaturated ketones where in the past there have been used α,β-unsaturated ketones. Secondly, in the step below where β,γ-unsaturated bromoketones (13 or 14) proceed to 1-bromo-N-formylnordihydrothebaine (morphinan) (17), in this process there are utilized super acids, such as trifluoromethane sulfonic, polyfluoroethane sulfonic and mixtures thereof, and also antimony pentafluoride and mixtures of hydrogen fluoride and antimony pentafluoride. An additional advantage of the present process is that oxide bridge closure is accomplished in the N-nor series bromonordihydrothebainone (18)→nordihydrocodeinone (21), thus affording ready access to either N-nor or N-methyl derivatives from the same intermediate 18. N-nor derivatives are of paramount importance in the synthesis of unnatural enantiomers of narcotic antagonists and the agonist-antagonist drugs. The N-methyl derivative, (+)-dihydrocodeinone(22), is a key intermediate which can be converted by established methods to unnatural (+)-codeine, morphine, thebaine and the corresponding enantiomers of all medically valuable opium derivatives of the morphinan type and related compounds.

In this specification, morphine-type means alkaloid compounds generally of the morphinan structure. Specially interesting are morphine and morphinan agonists and antagonists.

Grewe cyclization is a ring closure method and in the present disclosure utilizes bromine or other halogens as a blocking group. The deactivating influence of halogen on the phenolic ring is overcome by use of super acids in the Grewe cyclization (cf. J. Het. Chem., June 1974, 363).

Birch reduction of (−)-7a includes reduction with ammonia or lower amine and lithium (preferred) or other alkali metal.

The introduction of bromine in a 1:1 molar ratio folowed by alkali metal base served to close the oxide bridge. In a process proceeding from (+)-1-bromonordihydrothebainone (18) the bridge head nitrogen may be alkylated using an acid aldehyde, a lower aldehyde, or ketone such as theyl aldehyde or acetone.

The chart below is a synopsis of the sequence of steps.

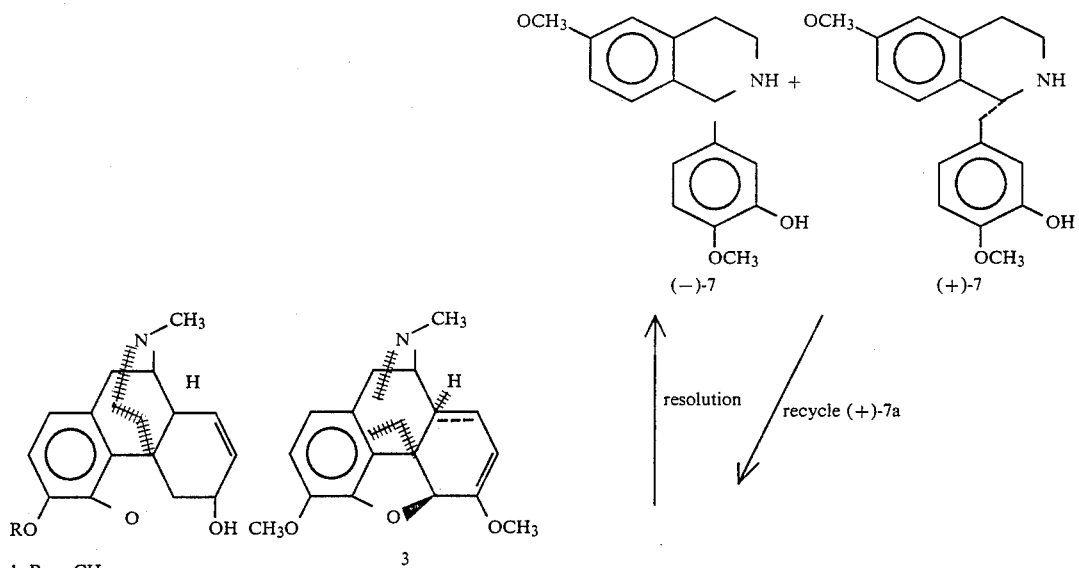

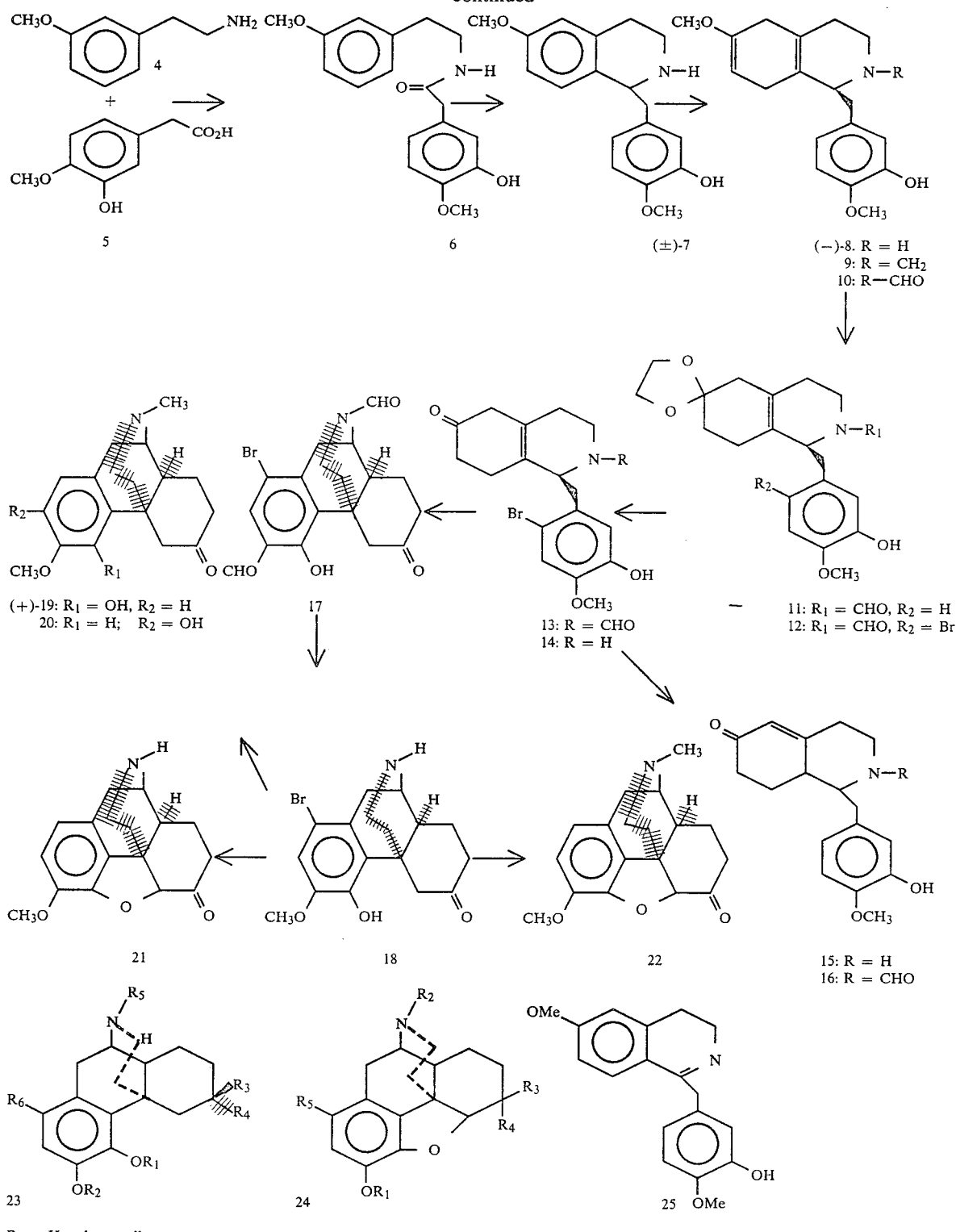

R₁ = H or lower alkoxy
R₂ = H or lower alkoxy
R₃ = H or OH or lower alkoxy
R₄ = H or OH or lower alkoxy
R₃ + R₄ = =O
R₅ = H, methyl or lower alkyl or lower alkmonoaryl
R₆ = H, Br or Cl R₁ = H or lower alkoxy
R₂ = H, methyl or lower alkyl or alkmonoaryl
R₃ = H, OH or lower alkoxy
R₄ = H, OH or lower alkoxy
R₃ + R₄ = =O
R₅ = H, Br or Cl An optional 7,8-double bond indicates coverage of the unnatural codeine series.

PRIOR ART STATEMENT

Rice, *J. of Organic Chemistry*, Vol. 45(15), July 18, 1980, pp. 3135-3137.

Rice, U.S. Pat. No. 4,368,326

With reference to the use of super acids, the invention encompasses such acids as trifluoromethane sulfonic, polyfluoroethane sulfonic, etc., and it is maintained that the use of these very strong acids overcomes the difficulty of use of acids, such as sulfuric, phosphoric, etc.

Relative to the compounds produced by alkylating the nitrogen bridge head, this reaction will work with lower amines and lower ketones. The utility of the products akin to nordihydrocodeinone (21) with N-alkylate are morhine agonists or antagonists. These compounds with the N-alkylate structure are denoted as tertiary amines and specially where N-methyl, N-ethyl, etc., are produced and the alkyl chain is $C_1$-$C_6$. Of the ketones, acetone and methyl ethyl ketone will operate. They are regarded as quite important for morphine overdose.

In general, as to utility, dihydrothebainone (19) is noted in *J. Med. Chem.*, 19:1171 (1976) and dihydrocodeinone (22) is a prescription drug on the market at present produced by Mallinckrodt, etc., as Hydrocodone.

As a general summary of the above chart, the following general description is made commencing with codeine (1). (+)-Dihydrothebainine (19), (+)-nordihydrocodeinone (21) and (+)-dihydrocodeinone (22) were synthesized in high overall yield from 3-methoxyphenethylamine (4), via the key intermediate (+)-1-bromonordihydrothebainone (18); the route utilized unprotected phenolic intermediates, involved directed Grewe-type cyclization and for 21 and 22, exploited novel oxide bridge closure in the N-nor series.

Natural (−)-codeine (1) continues to occupy a position of central importance among the medically valuable derivatives of the opium poppy as the most frequently prescribed analgesic-antitussive agent worldwide. Since the first total synthesis of (−)-codeine (1) and (−)-morphine (2), other successful routes, including Grewe-type and biomimetic approaches, have appeared. However, a practical total synthesis of these drugs has remained elusive. These and continuing efforts, together with possible shortages, underscore the desirability of securing a route which could render licit production of medical opiates independent of the natural and sole commercial source of these drugs. Since the reports that Grewe-type electrophilic cyclization of (+)-1-benzylhexahydroisoquinoline (9) afforded a 3% yield of the codeine precursor dihydrothebainone (19) (with isomeric 20 as the vastly predominant cyclization product), several groups have attempted to utilize this approach to codeine by introduction of a blocking substituent at the 1-position of the benzyl moiety in order to direct cyclization to the desired dihydrothebainone oxygenation pattern. Studies utilizing a 1-methyl substituent were successful in this regard. However, such an approach must also employ a readily removable group to be of value in synthesis of codeine and congeners, of course, not the case in the 1-methyl series. Substitution of bromine for methyl, unsuccessful hithertofore, would be ideal, since transformation of 4-hydroxymorphinans such as 19 to 22 (with the oxide bridge closed as in codeine) first involves bromination at C-1 of the morphinan system and later removal of the C-1 bromine atom by hydrogenolysis. Recent work describing conversion of (−)-dihydrothebainone [(−)-19] to (−)-codeine (1) (68% overall), via (−)-dihydrocodeinone, [(−)-22] and to (−)-thebaine (3), (an important minor opium alkaloid) in somewhat higher yield, renders any totally synthetic approach yielding 1-bromodihydrothebainone derivatives still more attractive. Such an approach which utilizes unprotected phenolic intermediates is short, experimentally simple, and affords (+)-dihydrothebainone (19), (+)-nordihydrocodeinone (21) and (+)-dihydrocodeinone (22) in high overall yield via the key intermediate (+)-1-bromonordihydrothebainone (18) is included in this disclosure. The sequence rests essentially on high yield preparation of $\beta,\gamma$-unsaturated bromoketone 13, that is converted by directed Grewe-type cyclization into (+)-1-bromo-N-formylnordihydrothebainone (17), and on the novel oxide bridge closure in the N-nor series, which optionally provides ready access to either N-methyl or N-nor derivatives.

Heating a mixture of amine 4 and pure acid 5 at 200° C. for 2 hr. under argon afforded amide 6 (95%, EtOAc). Cyclization of 6 (0.35 mol scale) with phosphorous oxychloride generated an aqueous solution of the 1,2-dehydro derivative of 7. The conversion of 6 to the 1,2-dehydro derivative of 7 is carried out under ring closure conditions in an organic solvent such as acetonitrile or other lower alkyl nitriles ($C_1$-$C_6$) containing phosphorous oxychloride. A preferred procedure utilizes a molar ratio of phosphorous oxychloride to 6 of greater than 1 and employs refluxing acetonitrile. When the reaction is complete, evaporation of the solvent and excess phosphorous oxychloride and addition of water to the residue gives an aqueous solution of the 1,2-dehydro derivative of 7.

Neutralization of pH 4–5 with concentrated aqueous $NH_3$ and reduction with an equimolar quantity of $NaCNBH_3$ or sodium borohydride in refluxing 45% MeOH (final concentration) for 1.5 hr. afforded pure (TLC) 7 (86%), mp 199.5°–201.5° C. Resolution of racemic tetrahydroisoquinoline 7 is accomplished by formation and fractional crystallization of diasterisomeric salts with optically active acids such as tartaric, mandelic and tartranilic acid, etc. The appropriate optically active base 7 is then regenerated and subjected the reaction sequence described herein to afford the corresponding morphinan derivatives with either the natural or unnatural morphine absolute configuration. The optically pure (+)-7 obtained showed m.p. 218.5°–220° C., and $[\alpha]_D^{23} = +38.1°$ (C 0.27, DMF). The corresponding enantiomer (−)-7 useful for preparing unnatural opiate derivatives showed m.p. 218°–219.5° C., and $[\alpha]_D^{23} = -37.7°$ (C 0.26 DMF).

The present invention also encompasses racemization of either enantiomer of 7 and derivatives so that, if desired, one enantiomer can be produced to the exclusion of the other by recycle of the racemate. Racemization can be accomplished by catalytic hydrogenation of the chiral 1-benzyl-1,2,3,4-tetrahydroisoquinoline with metal catalysts such as palladium, platinum, nickel and cobalt. Platinum and palladium catalysts in solvents such as alkanoic acids, ethers, and hydrocarbons are preferred. Simple filtration of the catalysts and workup by evaporation of the solvent affords the racemate in high chemical yield. Also, oxidation of 1-benzyltetrahydroisoquinolines, lower alkoxy and acyloxy derivatives with reagents such as N-chlorosuccinamide, sodium hypochlorite, sodium hypobromite, and lower alkyl hypochlorites and hypobromites, and treatment with base to give dehydro intermediate of type 25, followed by reduction with sodium cyanoborohydride or sodium borohydride, can be used to effect racemization of either enantiomer of 7. Synthesis of 25 and sodium cyanoborohydride reduction of 25 to (±)-7 was described above.

Birch reduction with lithium or sodium in liquid ammonia of 85 mmol of unpurified 7 with 1.92 g atom of lithium in 450 ml of liquid $NH_3$, 225 ml each of dry THF and 6-BuOH at $-55°$ to $-65°$ C. for 4 hrs., then at $-75°$ C. until no 7 remained by TLC (~1.5 h) afforded (90%) essentially pure (TLC) 8, mp 179.5° C. Refluxing unpurified 8 with 1.5 equivalents of pure PhOCHO, chloral in 10 volumes of EtOAc or in EtOCHO until TLC showed absence of 8 gave (94%) pure 10, which, as the N-formyl derivatives described below and others, existed as two distinct rotomers, as shown by NMR. This N-formyl derivatization introduces a protective group for the nitrogen in the subsequent steps of the reaction. Compound 7 or 8 may be N-methylated with methyl halide or sulfonate to give compound 9. Stirring a solution of 10 (25° C., 1 h.) in 20 volumes of dry THF containing 1% (v/v) $CH_3SO_3H$ and 3 molar equivalents of ethylene glycol generated a solution of ketal 11 (quantitatively by TLC) which was treated at 0°-5° C. during 0.5 h with 1.05 equivalents of recrystallized N-bromoacetamide (NBA) to afford essentially pure bromoketal 12 after neutralization with $NH_3$ gas, solvent evaporation and workup with $CHCl_3$—$H_2O$. Bromoketal 12 was most efficiently deketalized in 6 volumes of 5:1 88% $HCO_2H$—$H_2O$ (25° C., 1 h) followed by $CHCl_3$-aqueous $NaHCO_3$ workup to afford 13, IR ($CHCl_3$) 1717 (C=O) and 1665 (NCHO) $cm^{-1}$ in 90% yield from 10.

Bromoketone 13 underwent Grewe-type cyclization to (+)-1-bromo-N-formylnordihydrothebainone (17), in 60% isolated yield with dry $CF_3SO_3H$ for 24 hrs. at 25° C. until 13 had essentially disappeared by TLC. Synthetic (+)-17 showed mp 216.5°-218.5° C. and $[\alpha]_D^{23} = 152°$ (c 0.5, $CHCl_3$) immediately after dissolving in chloroform. After standing overnight in chloroform at 25° C., the compound showed $[\alpha]_D^{23} = +189°$ due to equilibration of the rotamers about the C—N bond of the N-formyl group. Also, isomerization of 13 occurred during cyclization to give (TLC) the α,β-unsaturated bromoketone 16. Pure 16 afforded (TLC) only traces of morphinan 17, and β,γ-unsaturated ketone 13 under the conditions used to cyclize 13 to (+)-17. Treatment of pure morphinan (+)-17 under these conditions gave no 13 or 16 (TLC); the acid catalyzed equilibrium of 13 and 16 lies nearly exclusively toward the side of the latter, which undergoes little, if any, morphinan cyclization under these conditions. Refluxing isolated (+)-17 in 10:1 MeOH-37% aqueous HCl for 18 h. afforded (+)-1-bromonordihydrothebainone (18), which was easily isolated as the 1:1 fumarate salt, mp 244° C. (+)-Dihydrothebainone (19), mp 148°-152° C. was obtained directly and quantitatively from (+)-17 by hydrolysis as above, evaporation to dryness, and hydrogenation of the residue in 2N AcOH containing 50 mg 10% Pd/C, 0.1 ml of 37% HCHO and 5 mmol of NaOAc per mmol of 17, followed by workup with $CHCl_3$-aqueous $NH_3$. Bromination (1.1 mol of $Br_2$, 25° C., 2H) of an AcOH or $CHCl_3$ solution of the dry residue from hydrolysis of 17, evaporation, treatment of the residue with $CHCl_3$-1N NaOH and hydrogenation as above without addition of HCHO afforded an 80% yield (from (+)-17) of (+)-nordihydrocodeinone (21), mp 151°-153° C. (as hydrate from $EtOAc$-$H_2O$). This is the first example of closure of the oxide bridge in the basic N-nor series and is of potential interest in the synthesis of narcotic antagonists. When (+)-17 was treated as in the preparation of (+)-21, and 0.1 ml of 37% HCHO/mmol of (+)-17 was added to the hydrogenation medium (+)-dihydrocodeinone (22), mp 194°-196° C. was easily isolated in 79% yield from 17.

This straightforward total synthesis of (+)-dihydrothebainone (19), (+)-nordihydrocodeinone (21), and (+)-dihydrocodeinone (22) in high overall yields respectively, from readily available 3-methoxyphenethylamine (4) requires isolation of only 6 intermediates. These are directly obtained sufficiently pure for further transformation. In view of these results, the high yielding conversion of (−)-19 to (−)-thebaine (3) and (−)-codeine (1) discussed above and the facile O-demethylation of the latter to (−)-morphine (2), a practical total synthesis of both enantiomers of these alkaloids (and the thebaine based drugs) have resulted. Compounds of the general structures 23 and 24 are prepared by conventional techniques from process compounds 18, 19, 21 and 22.

The term "super acid" or "super acids" is defined to mean and include in this specification and claims the following: All protic acids stronger than 100% sulfuric, thus in this group are perchloric acid $HClO_4$, fluorosulfuric $HSO_3F$, and trifluoromethane sulfonic acid $CF_3SO_3H$, as well as trifluoroethane sulfonic acid. A convenient review incorporating this definition is found in Science, Vol. 26, No. 4414, Oct. 5, 1979, pages 13-20.

I claim:

1. In the preparation of compounds 23 and 24

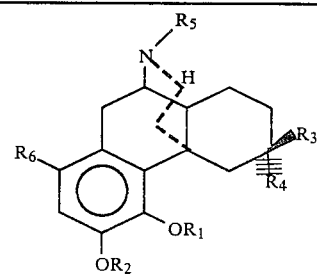

23 wherein
$R_1$ = H or lower alkoxy and
$R_2$ = H or lower alkoxy and
$R_3$ = H or OH or lower alkoxy and
$R_4$ = H or OH or lower alkoxy and
$R_3 + R_4 =$ =O and
$R_5$ = H, methyl or lower alkyl or lower alkmonaryl and
$R_6$ = H, Br, or Cl

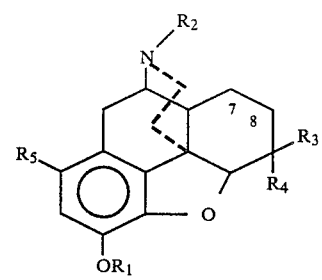

24

-continued wherein
R₁ = H or lower alkoxy and
R₂ = H, methyl or lower alkyl or alkmonoaryl and
R₃ = H, OH or lower alkoxy and
R₄ = H, OH or lower alkoxy and
R₃ + R₄ = =O and
R₅ = H, Br or Cl and
An optional 7,8-double bond indicates coverage of the unnatural codeine series.

by a total synthesis method, the steps which comprise:
(a) heating a mixture of an amine compound of the formula 4

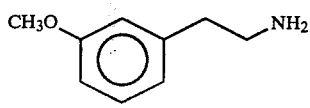
4 and pure acid compound, formula 5

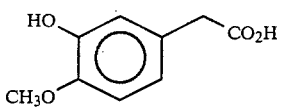
5 at 200° C. for about 2 hours under argon or other inert gas to obtain amide compound 6 of the following formula

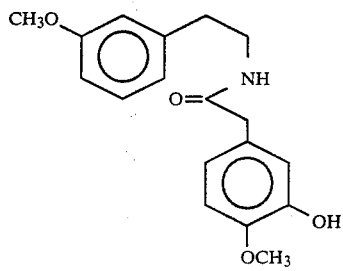
6

(b) contacting compound 6 with phosphorous oxychloride to produce the 1,2-dehydro derivative of compound 7 shown below:

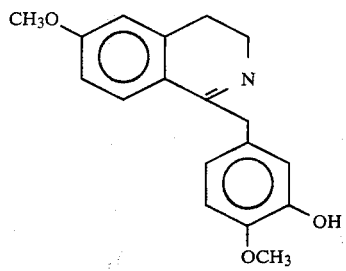

which need not be isolated;
(c) neutralizing the 1,2-dehydro derivative of compound 7 with aqueous ammonia and reducing with sodium cyanoborohydride or sodium borohydride to give racemic 7 which is then resolved by optically active acids to the compound tetrahydroisoquinoline (+)-7 to (−)-7

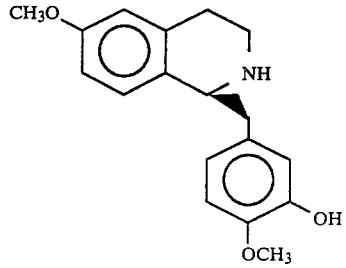

(d) treating of (−)-7 with lithium or sodium in liquid ammonia as a reducing agent to give hexahydroisoquinoline, compound (−)-8

[structure 8]

and formylating compound (−)-8 to give 10

[structure 10]

and introducing a protective group for the nitrogen in the subsequent steps of the reaction where the reagent for formylation of 8 to 10 is phenylformate chloral or ethyl formate
(e) alternately, N-methylating compound (−)-7 or (−)-8 by treatment with methyl halides or sulfonate to give the N-methyl derivative of 7 or compound 9

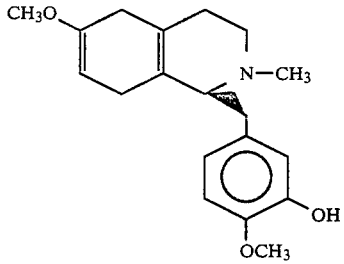
9

(f) contacting compound 10 with ethylene glycol in dry methane sulfonic acid in dry tetrahydrofuran to afford the ketal product, 11

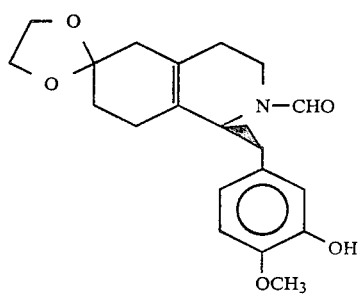

(g) brominating of ketal 11 with N-bromoacetamide (NBA) to give bromo ketal 12

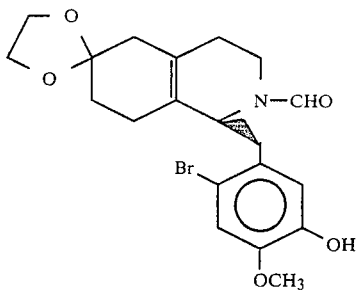

(h) deketalizing bromo ketal 12 with aqueous formic acid to yield beta, gamma unsaturated ketone 13

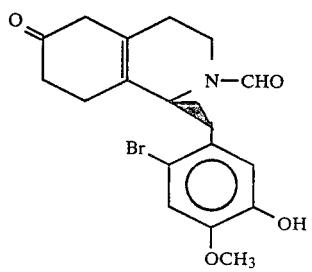

(i) treating beta, gamma unsaturated bromo ketone 13 with a super acid alone or with ammonium fluoride HF complex with trifluoromethanesulfonic acid to give 1-bromo-N-formylnordihydrothebainone (+)-17

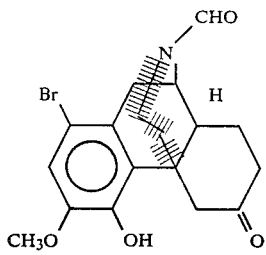

(j) acid hydrolyzing 1-bromo-N-formylnordihydrothebainone (+)-17 with aqueous acid and methanol to give the intermediate 1-bromonordihydrothebainone, compound (+)-18

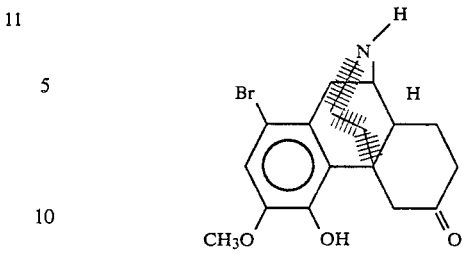

(k) converting intermediate (+)-18, 1-bromonordihydrothebainone, to dihydrothebainone (+)-19, a codeine precursor by hydrogenation in the presence of formaldehyde with palladium on carbon catalyst in 2-normal (2N) acetic acid containing sodium acetate; or (l) treating intermediate (+)-18 with bromine in acetic acid or chloroform followed by treating with sodium hydroxide to close the oxide bridge and afford as an intermediate (+)-1-bromonordihydrocodeinone which need not be isolated but is hydrogenated in the presence of formaldehyde to give dihydrocodeinone (+)-22, a codeine precursor or

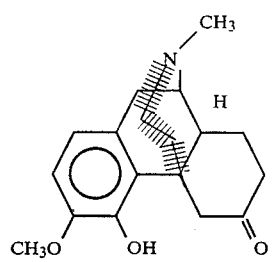

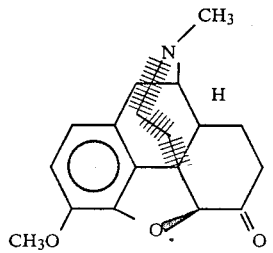

(m) alternately, converting compound (+)-18 into compound (+)-21, nordihydrocodeinone

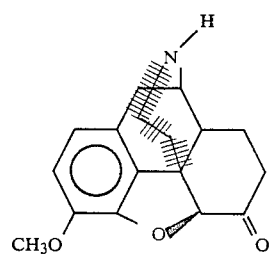

by bromination in acetic acid followed by treating with an aqueous base to close the oxide bridge, and hydrogenating the unisolated intermediate with palladium on carbon catalyst in 2-norman (2N) acetic acid containing sodium acetate.

* * * * *